United States Patent [19]

Ito

[11] Patent Number: 4,715,708
[45] Date of Patent: Dec. 29, 1987

[54] PARTICLE ANALYZING APPARATUS WITH INDEX PROJECTING OPTICAL SYSTEM FOR DETECTING A FOCUSING STATE OF THE MEASURING SYSTEM

[75] Inventor: Yuji Ito, Chigasaki, Japan

[73] Assignee: Canon Kabushiki Kaisha, Tokyo, Japan

[21] Appl. No.: 867,496

[22] Filed: May 28, 1986

[30] Foreign Application Priority Data

Jun. 5, 1985 [JP] Japan .............................. 60-121885

[51] Int. Cl.⁴ ......................... G01N 21/01; G03B 3/10
[52] U.S. Cl. .................................... 356/72; 250/201; 356/73; 356/318; 356/339
[58] Field of Search .................. 356/72, 73, 317, 318, 356/339, 39; 250/201 AF

[56] References Cited

U.S. PATENT DOCUMENTS 4,595,271 6/1986 Suda et al. .................. 250/201 AF Primary Examiner—Vincent P. McGraw
Attorney, Agent, or Firm—Fitzpatrick, Cella, Harper & Scinto

[57] ABSTRACT

In an apparatus for analyzing a particle flowing in a flow section of a flow cell, at least two non-parallel index beams are projected onto the flow cell to detect a focusing state of a measuring optical system with respect to the flow section, the beams reflected by first and second walls of the flow cell are detected, and the obtained output pattern is used to determine the focusing state.

11 Claims, 10 Drawing Figures

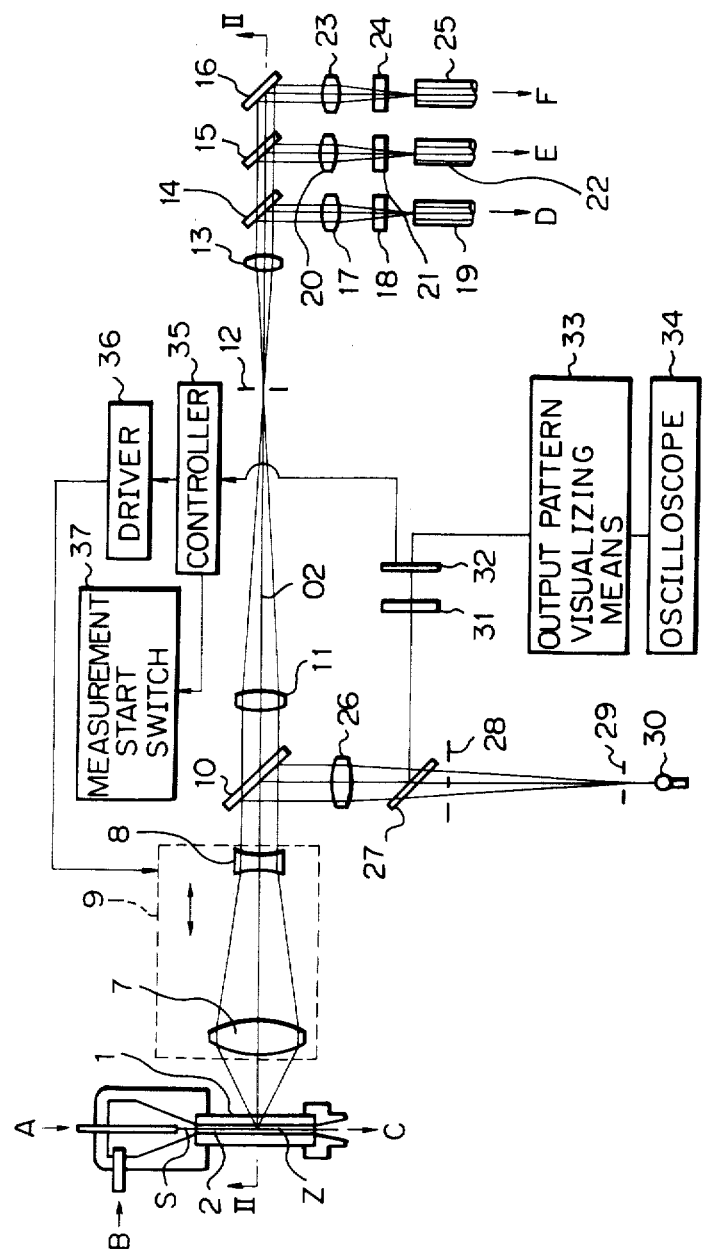

Fig. 1-(b)
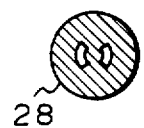
Fig. 1-(c)       Fig. 1-(d)
   
Fig. 1-(e)       Fig. 1-(f)
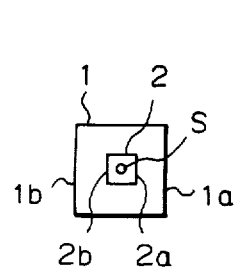   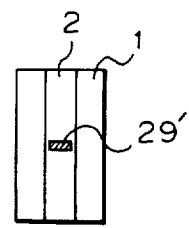

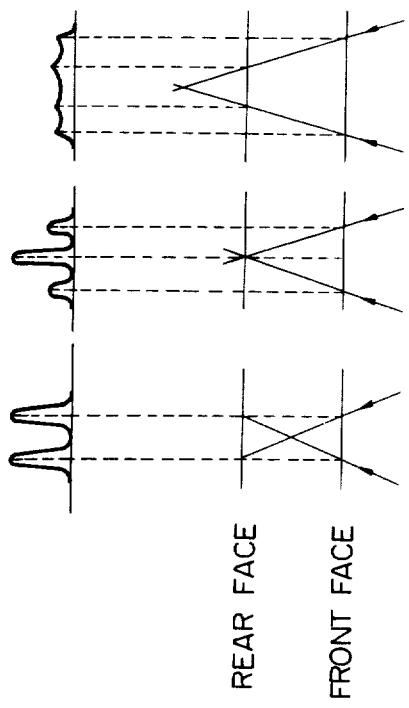
*Fig.3-(a) Fig.3-(b) Fig.3-(c)*
REAR FACE
FRONT FACE
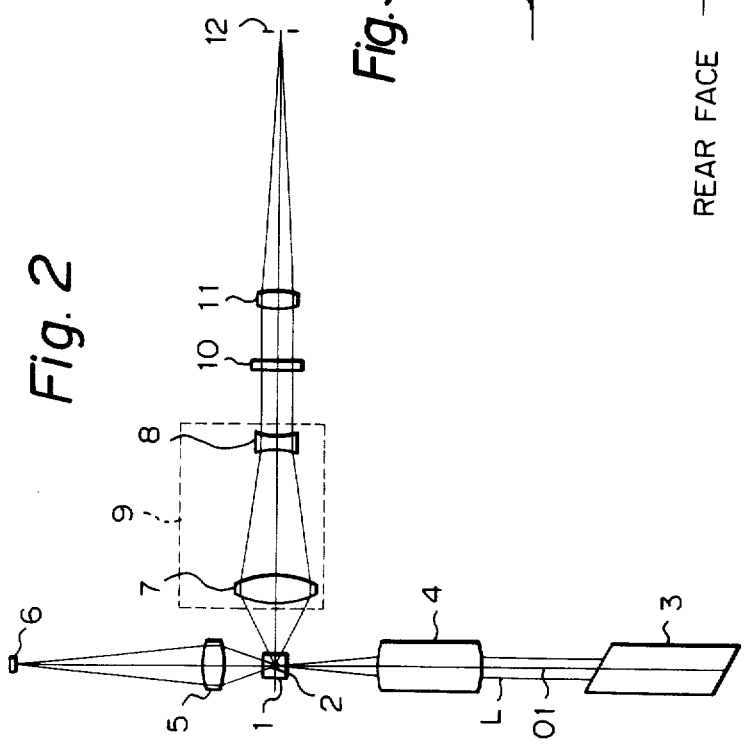
*Fig. 2*

4,715,708

PARTICLE ANALYZING APPARATUS WITH INDEX PROJECTING OPTICAL SYSTEM FOR DETECTING A FOCUSING STATE OF THE MEASURING SYSTEM

BACKGROUND OF THE INVENTION

1. Field of the Invention

The present invention relates to a particle analyzing apparatus capable of detecting a focusing state with respect to a flow section of a measuring optical system.

2. Related Background Art

In a conventional particle analyzing apparatus employed, for example, in a flow cytometer, a particle to be examined, such as a blood cell, suspended in a sheath liquid and flowing through a flow section of a minute rectangular cross section of for example 200 μm ×200 μm at the center of a flow cell, is irradiated with light such as a laser beam, and information on the particle, such as shape, dimension, refractive index, etc., can be obtained by measuring light forward or laterally scattered thereby. Also in a specimen which can be dyed with a fluorescent material, important information for particle analysis can be obtained by measuring the fluorescent light in the laterally scattered light, which is scattered in a direction substantially perpendicular to the irradiating light.

For achieving a correct measurement in a flow cytometer or the like, the light beam has to be correctly focused on the particle to be examined or on the vicinity thereof by means of a measuring objective lens, in order to avoid pseudo signals coming from objects other than the particle to be examined, and, for this purpose, the measuring objective lens requires exact focusing. In a conventional apparatus, however, focusing is conducted manually with a standard sample under visual observation prior to the actual measurement. However, such a focusing operation is not only cumbersome, but is also inaccurate due to differences between examiners.

Also an eventual aberration in focusing, appearing in the course of measurement, cannot be detected. Consequently, since the presence of pseudo signals in the course of measurement cannot be detected, a certain ambiguity about the reliability of the obtained data remains.

In addition, the focusing operation has to be repeated whenever a nozzle or the flow cell is replaced and an additional time is required for this focusing operation. On the other hand, a very weak fluorescent signal has to be intensified to allow fluorescent measurement, and, for this purpose, it has been proposed to employ a photomultiplier as the detector for the fluorescent light, in order to improve the light-emitting efficiency of the fluorescent material. In addition to the above, increasing the power of the irradiating light source and improving the light condensing power of the measuring objective lens have also been proposed. The condensing power of the objective lens can be improved by the use of a larger aperture, but this leads to a smaller focal depth. With such a smaller focal depth, even a slight change in the distance between the flow section and the objective lens gives rise to introduction of noise signals from other objects, thereby prohibiting exact measurement. In this manner, the conventional apparatus not only requires a cumbersome focusing operation, but also cannot provide a sufficient precision of analysis due to an insufficient intensity of the fluorescent signal.

In order to eliminate the above drawbacks, the present applicant filed copending U.S. Ser. No. 818,263 In the apparatus of this copending application, a focusing light beam irradiates front and rear walls of a flow section of a flow cell along an optical path oblique to the optical axis of a measuring objective lens. The beams reflected by the front and rear walls are received by devided elements of a photosensor. A focusing state is obtained by simultaneously moving both the measuring objective lens and a focusing optical system until output signals, from the divided elements are the same.

In this apparatus, a sufficiently precise focusing state is normally obtained. However, since the focusing state is measured by a comparison between the output signals from the divided elements, when the interior of the flow section of the flow cell is soiled to a considerable degree and the intensity of the reflected light is thus decreased, it is difficult to compare the output signals. In addition, when a difference occurs in the reflectances between the front and rear walls of the flow sections due to the soiled surfaces thereof, correct detection cannot be performed.

SUMMARY OF THE INVENTION

It is an object of the present invention to provide a particle analyzing apparatus capable of correctly performing focusing and high-precision analysis.

It is also an object of the present invention to provide a particle analyzing apparatus wherein focusing is performed automatically, and measurement is initiated automatically after the focusing.

BRIEF DESCRIPTION OF THE DRAWINGS

The accompanying drawings show a particle analyzing apparatus according to an embodiment of the present invention, in which:

FIG. 1-(a) is a side view of an optical system;

FIGS. 1-(b) to 1-(f) show respective constituent members of the system in FIG. 1-(a), in which FIGS. 1-(b) and 1-(c) show an aperture diaphragm, FIG. 1-(d) shows an array sensor, and FIGS. 1-(e) and 1-(f) show a flow cell;

FIG. 2 shows the optical system in FIG. 1-(a) from above; and

FIGS. 3-(a), 3-(b) and 3-(c) are schematic views showing the distribution of light images on divided elements.

DETAILED DESCRIPTION OF THE PREFERRED EMBODIMENT

An embodiment of the present invention will be described in detail with reference to the accompanying drawings.

FIGS. 1-(a) to 1-(f) and FIG. 2 are views of a particle analyzing apparatus, in which FIG. 1-(a) shows a flow cell and a flow section in a state wherein a particle S to be detected flows in the plane of the drawing, of a detecting optical system for the laterally scattered light, and of a focusing optical system; and FIG. 2 is a sectional view taken along the line II—II of FIG. 1-(a) showing part of the flow section in a state wherein the particle S flow is in a direction perpendicular to the plane of the drawing, of an optical laser irradiating system, and of the forward and laterally scattered light detecting optical system. Sample liquid and sheath liquid inlet ports A and B are connected to a flow cell 1. The particle S, on which hydrodynamic focusing has been performed, flows in a sheath-liquid fast laminar flow from the orifice of the flow cell 1. A laser beam irradiates the particle S at the flow section 2 of the flow cell 1, and the particle S is discharged from a distal end C of the flow cell 1 as a drain. The flow cell 1 has outer walls 1a and 1b, and the flow section 2 has front and rear inner walls 2a and 2b, as shown in FIG. 1-(e).

A laser beam L emitted from a laser unit 3 passes the flow section 2 of the flow cell 1, and a condenser lens 5 along an optical axis 01 through an imaging lens system 4, and reaches a photoelectric detector 6.

In a direction substantially perpendicular to a central axis Z of the flowing direction of the particle S and the optical axis 01 of the laser beam L, there are provided, in succession, a measuring objective lens system 9 containing a convex lens 7 and a concave lens 8, a wavelength selecting means 10 such as a dichroic mirror, a convex lens 11, a diaphragm 12, a convex lens 13, wavelength selecting means 14 and 15, and a reflecting mirror 16. On optical paths of light beams reflected by the wavelength selecting means 14 and 15 and the reflecting mirror 16 proivded obliquely with respect to an optical axis 02 of the laterally scattered light, there are respectively provided a convex lens 17, a barrier filter 18, and one end of an optical fiber 19; a convex lens 20, a barrier filter 21, and one end of an optical fiber 22; and a convex lens 23, a barrier filter 24, and one end of an optical fiber 25. Photoelectric detectors (not shown) are respectively connected to the other ends of the optical fibers 19, 22, and 25. Photomultipliers capable of detecting very weak light by amplification are usually used as the photoelectric detectors.

On the opposite side of the wavelength selecting means 10, 14 and 15, oblique with respect to the optical axis 02, there are provided, in succession, a convex lens 26, a half mirror 27, an aperture diaphragm 28 having two apertures (preferably of the same shapes and at symmetrical positions with respect to the optical axis) as shown in FIG. 1-(b), an aperture diaphragm 29 having one slit as shown in FIG. 1-(c), and a focusing light source 30. The aperture diaphragm 28 is provided closer to the light source 30 than the half mirror 27 is. A band-pass filter 31 and an array sensor 32 shown in FIG. 1-(d) are arranged in succession on the other side of the half mirror 27 which is provided obliquely in the optical axis.

Two pairs of cylindrical orthogonal lenses are normally used as the imaging lens system 4. The laser beam L formed by the system 4 is a beam having any major and minor axes, and irradiates the particle S. In the light of the laser beam L, light scattered by the particle S in the forward direction is received by the photoelectric detector 6 through the condenser lens 5, to measure properties of the particle S. The intensities of the output signals from the photoelectric detector 6 are related to the size of the particle S. Therefore, the forward scattered light is normally used to determine the size of the particle S.

For a particle S dyed with one of various fluorescent materials, fluorescent light and/or light scattered in the lateral direction is focused to a diaphragm 12 by the measuring objective lens system 9 and the convex lens 11. The diaphragm 12 is optically conjugate with the particle S. After the laterally scattered light and/or fluorescent light passes through the diaphragm 12, a measurement signal with a small noise component can be obtained. In order to measure the particle S dyed with a fluorescent material, an Ar+ laser beam with a wavelength of 488 nm is usually employed, and the particle S emits green or red fluorescent light. For example, a particle S dyed with PI (Propidium Iodide) for detection of a DNA content emits red fluorescent light. A particle S dyed with an FITC (Fluorescein Isothiocyanate) for detection of cell membrane surface antigens emits green fluorescent light. A DNA in a particle S dyed with acridine orange emits red fluorescent light. It is also known that the amount of light scattered 90° by the wavelength of the Ar+ laser reflects the granularity of the interior of the particle S.

Recently, various fluorescence probes, i.e., fluorescent materials which can be combined with nucleic acid or proteins in a cell, have been developed and are used in accordance with various applications. Usually, the laterally scattered light is separated into beams in accordance with its wavelengths, thereby obtaining respective measurement values. More specifically, after passing through the diaphragm 12, a light beam is converted into a parallel beam by the convex lens 13, and is divided by the wavelength selecting means 14 (e.g., a dichroic mirror of suitable spectral characteristics), into laterally scattered light and fluorescent light. The laterally scattered light is detected by the corresponding photoelectric detector through the convex lens 17, the barrier filter 18, and the optical fiber 19, to determine the granularity of the particle S. When an Ar+ laser beam with a wavelength of 488 nm is used as the laser unit, the wavelength selecting means 14 must transmit light beams with a wavelength longer than 488 nm, and the barrier filter 18 must be a band-pass filter which transmits light beams with a wavelength of 488 nm.

On the other hand, after the fluorescent light passes through the wavelength selecting means 14, it is divided into, e.g., green and red fluorescent light by means of the wavelength selecting means 15 (e.g., a dichroic mirror which reflects green light beams and transmits red light beams). The green fluorescent light is detected by the corresponding photoelectric detector through the convex lens 20, the barrier filter 21 as a band-pass filter which transmits only green light beams, and an optical fiber 22. Similarly, the red fluorescent light is detected by the corresponding photoelectric detector through the reflecting mirror 16, the convex lens 23, the barrier filter 24 as a band-pass filter which transmits only red light beams, and an optical fiber 25. Together, the detection results determine biochemical properties of the particle S.

The wavelength selecting means 15 for selecting fluorescent light is usually composed of a dichroic mirror of, e.g., green and red, but a spectral prism or a diffraction grating capable of continuous separation of light wavelengths can also be employed. In addition, the reflecting mirror 16 can be a dichroic mirror which reflects only red light beams.

A means for detecting the focusing state of the measuring objective lens system 9 will now be described. The wavelength of the focusing light source 30 is preferably different from that of the laser beam unit 3 or of the fluorescent light in order to avoid an adverse influence on the measurement of scattered light in the flow section 2, and is preferably selected in the infrared range. In this case, the light source 30 emits infrared beams, and the wavelength selecting means reflects the infrared beams and transmits visible light beams.

The light beams passing through the slit-like aperture diaphragm 29 shown in FIG. 1-(c) are focused to two beams by the aperture diaphragm 28 shown in FIG. 1-(b), and are thereafter reflected by the wavelength selecting means 10 to the side of the objective lens system 9 through the half mirror 27 and the convex lens 26. The beams are then focused onto the flow section 2 of the flow cell 1 by the objective lens system 9, and are reflected as index beams by the front and rear walls 2a and 2b of the flow section 2, thereby providing a total of four reflected beams. The reflected beams are refracted by the objective lens system 9, and are reflected by the wavelength selecting means 10 and the half mirror 27 through the convex lens 26, thereby forming an image of the aperture diaphragm 29 on the array sensor 32 through the barrier filter 31, as shown in FIGS. 3-(a) to 3-(c). The barrier filter 31 transmits only light beams of a wavelength falling within the wavelength range of the light source 30, so that an adverse effect of the disturbance can be minimized.

The aperture diaphragm 29 has a slit of a length which allows a beam passing through it to radiate on the flow section 2. Therefore, a slit 29' is projected on the inside of flow section 2, as shown in FIG. 1-(f). The array sensor 32 is positioned at the focal point of the convex lens 26. When the objective lens system 9 is in the focusing state, the array sensor 32 is optically conjugate with the center of the flow section 2, i.e., with an intermediate portion between the front and rear walls 2a and 2b. The array sensor 32 and the aperture diaphragm 29 are located at optically equivalent positions. When the objective lens system 9 is in the focusing state and the focal point is located at the center of the flow section 2, thin focusing index beams irradiate the front and rear walls 2a and 2b of the flow section 2 and are reflected thereby to be superposed on each other, as shown in FIG. 3-(a), thereby providing a pattern signal with two clear peaks from the array sensor 32. On the other hand, when the objective lens system 9 is in the non-focusing state and the focal point is located on either the front or rear walls 2a or 2b of the flow section 2, three peaks are formed on the array sensor 32. When the focal point is not located on the flow section 2 at all, a pattern signal having a width as shown in FIG. 3-(c) is obtained.

After measurement is initialized using a flow cell 1 with a clean flow section 2, as repeated measurements are taken, the interior of the flow section 2 is soiled with the sample liquid, and the front and rear reflecting surfaces of the front and rear walls 2a and 2b of the flow section 2 are thus no longer clean. In this state, the intensity of reflected light is decreased. When the photoelectric detector for receiving reflected light from the flow section 2 consists of divided elements and the focusing state is detected in accordance with the outputs from the detector, if the intensity of the reflected light is decreased, comparison of the outputs becomes difficult. According to the present embodiment, however, only the pattern of the signal on the array sensor 32 is monitored, and thus the focusing state can be detected without being substantially influenced by the intensity in the reflected light.

When a focusing detection signal obtained in this manner is displayed on, e.g., an oscilloscope by an output pattern visualizing means 33, the focusing state can be obtained by manually shifting the objective lens system 9. Automatic focusing can be achieved by providing a driving unit, such as a servo motor dirver 36, with the focusing detection signal driving a focusing system including the objective lens system 9 along the optical axis until a signal wavelength having two peaks is obtained on the array sensor 32, and stopping the driver at the position which provides the focused signal. A further improvement in apparatus operability can be attained in this manner.

In addition, inaccurate measurement caused when the objective lens system 9 is not focused can be avoided by automatically turning on a measurement start switch 37 in response to a signal indicating that the driving mechanism for the focusing system is stopped or in response to an output signal from the array sensor 32 indicating an in-focus state, and thereafter initiating measurement with the particle analyzing apparatus. The flow cell 1 can be manually or automatically driven by the signal from the array sensor 32 instead of driving the objective lens system 9 and the optical focusing system, thereby performing focusing. Note that the number of apertures in the aperture diaphragm 28 is not limited to two, but can be more.

In the above description, focusing is performed using reflection on the front and rear walls 2a and 2b of the flow section 2. However, focusing can be performed using reflection on the external walls 1a and 1b, and an intermediate plane as the focal plane.

A total internal reflecting mirror can be used in place of the wavelength selecting means 10. In this case, the total reflecting mirror is inserted in the optical path to perform alignment, and is pivoted or linearly moved outside the optical path during measurement.

In the above description, the present apparatus is applied to focus detection. However, the present apparatus can also be applied to alignment detection. In other words, alignment can be detected in accordance with an error in a central value of the output signal waveform from its predetermined central position value.

What is claimed is:

1. A particle analyzing apparatus comprising:
    an irradiating optical system for emitting a particle analyzing beam onto a particle to be examined, the particle flowing in a flow section of a flow cell;
    a measuring optical system for measuring light obtained by scattering of the particle analyzing beam by the particle to be examined, and/or fluorescent light obtained therefrom;
    an index projecting optical system for projecting at least two non-parallel index beams for detecting a focusing state of said measuring optical system with respect to said flow section of said flow cell; and
    a focusing state detection system for detecting the focusing state in accordance with an output pattern obtained by receiving the focusing detection beams reflected by first and second walls of said flow cell.

2. An apparatus according to claim 1, wherein said first and second walls are front and rear walls of said flow section.

3. An apparatus according to claim 1, wherein at least two light-transmitting sections are provided in said index projecting optical system to be symmetrical with respect to an optical axis thereof.

4. An apparatus according to claim 1, wherein the index beams have slit-like sections at an intermediate position between said first and second walls.

5. An apparatus according to claim 1, wherein said measuring optical system and said focusing state detection system commonly use an objective lens opposing said flow cell.

6. An apparatus according to claim 1, wherein a wavelength region of a beam received by said measuring optical system and a wavelength region of a beam received by said focusing state detection system are different.

7. An apparatus according to claim 6, wherein optical paths of said measuring optical system and said focusing state detection system are split by a wavelength selecting optical splitting member.

8. An apparatus according to claim 1, wherein optical paths of said measuring optical system and said focusing state detection system are split by a pivot mirror, and said pivot mirror is located in the optical path of said focusing state detection system in either a focusing state detection mode or a measuring mode, and is outside the optical path otherwise.

9. A particle analyzing apparatus comprising:
   an irradiating optical system for emitting a particle analyzing beam onto a particle to be examined, the particle flowing in a flow section of a flow cell;
   a measuring optical system for measuring light obtained by scattering of the particle analyzing beam by the particle to be examined, and/or fluorescent light obtained therefrom;
   an index projecting optical system for projecting at least two non-parallel index beams for detecting a focusing state of said measuring optical system with respect to said flow section of said flow cell;
   a focusing state detection system for detecting the focusing state in accordance with an output pattern obtained by receiving the focusing detection beams reflected by first and second walls of said flow cell; and
   means for visualizing the output pattern.

10. A particle analyzing apparatus comprising:
    an irradiating optical system for emitting a particle analyzing beam onto a particle to be examined, the particle flowing in a flow section of a flow cell;
    a measuring optical system for measuring light obtained by scattering of the particle analyzing beam by the particle to be examined, and/or fluorescent light obtained therefrom;
    an index projecting optical system for projecting at least two non-parallel index beams for detecting a focusing state of said measuring optical system with respect to said flow section of said flow cell;
    a focusing state detection system for detecting the focusing state in accordance with an output pattern obtained by receiving the focusing detection beams reflected by first and second walls of said flow cell; and
    a drive mechanism for changing the focusing state of said measuring optical system in accordance with an output from said focusing state detection system.

11. An apparatus according to claim 10, comprising means for initializing measurement after said drive mechanism is stopped.

* * * * *

UNITED STATES PATENT AND TRADEMARK OFFICE
CERTIFICATE OF CORRECTION

PATENT NO. : 4,715,708
DATED : December 29, 1987
INVENTOR(S) : YUJI ITO

It is certified that error appears in the above-identified patent and that said Letters Patent is hereby corrected as shown below:

COLUMN 1

Line 21, "forward" should read --forwardly--.

COLUMN 2

Line 8, "devided" should read --divided--.
Line 11, "signals," should read --signals--.
Line 64, "forward" should read --forwardly--.

COLUMN 3

Line 21, "proivded" should read --provided--.
Line 55, "forward" should read --forwardly--.
Column 5, line 65, "signal" should read -- signal, --.

Signed and Sealed this

Fifth Day of July, 1988

Attest:

DONALD J. QUIGG

*Attesting Officer*  *Commissioner of Patents and Trademarks*